US007213016B1

(12) United States Patent
Barmakian

(10) Patent No.: US 7,213,016 B1
(45) Date of Patent: May 1, 2007

(54) SYSTEM AND METHOD FOR MANAGING ADVANCE DIRECTIVES

(76) Inventor: Joseph Barmakian, 258 E. Dudley Ave., Westfield, NJ (US) 07090

( * ) Notice: Subject to any disclaimer, the term of this patent is extended or adjusted under 35 U.S.C. 154(b) by 483 days.

(21) Appl. No.: 10/813,353

(22) Filed: Mar. 30, 2004

(51) Int. Cl.
G06F 17/30 (2006.01)
(52) U.S. Cl. .................. 707/3; 707/8; 707/9; 707/10
(58) Field of Classification Search ........... 707/1–10
See application file for complete search history.

(56) References Cited

U.S. PATENT DOCUMENTS

| 6,157,914 | A | 12/2000 | Seto et al. ............... 705/3 |
| 6,574,742 | B1 | 6/2003 | Jamroga et al. ......... 713/400 |
| 6,604,115 | B1 | 8/2003 | Gary, Jr. et al. ....... 707/104.1 |
| 2001/0034617 | A1 | 10/2001 | Kimata ................... 705/3 |
| 2001/0041991 | A1 | 11/2001 | Segal et al. ............. 705/3 |
| 2002/0029264 | A1 | 3/2002 | Ogino et al. ........... 709/223 |
| 2002/0103675 | A1 | 8/2002 | Vanelli ................... 705/3 |
| 2002/0169638 | A1 | 11/2002 | Rodriguez-Cue ....... 705/3 |
| 2002/0188467 | A1 | 12/2002 | Eke ........................ 705/2 |
| 2002/0196141 | A1 | 12/2002 | Boone et al. ............ 340/540 |
| 2003/0040939 | A1* | 2/2003 | Tritch et al. ............ 705/2 |
| 2003/0101081 | A1 | 5/2003 | Putnam et al. ......... 705/4 |
| 2003/0120527 | A1 | 6/2003 | Palomo et al. ......... 705/7 |

FOREIGN PATENT DOCUMENTS

| WO | WO01/06436 | 1/2001 |
| WO | WO01/99027 | 12/2001 |
| WO | WO02/37235 | 5/2002 |

* cited by examiner

Primary Examiner—Isaac Woo
(74) Attorney, Agent, or Firm—Thomas L. Adams

(57) ABSTRACT

A system and method can store and retrieve advance directives with a database that is coupled to a communications system. The database is arranged to register and store information about a service provider in anticipation of future creation of advance directives that will come into at least the temporary possession of the service provider. The database is arranged to store information supplied by the service provider and about a person and the person's advance directive. The communications system is operable in response to a request by the service provider to automatically transmit information about one or more advance directives that were stored in the database by the service provider.

34 Claims, 3 Drawing Sheets

SYSTEM AND METHOD FOR MANAGING ADVANCE DIRECTIVES

BACKGROUND OF THE INVENTION

1. Field of the Invention

The present invention relates to systems and methods for handling data, and in particular, to techniques and equipment for dealing with advance directives.

2. Description of Related Art

An advance directive is a type of written or verbal instruction about health care to be provided if a person becomes unable to make decisions regarding his or her medical treatment. As used herein the term advance directives shall include, but not be limited to, health care proxies, living wills, a do not resuscitate (DNR) instruction, or information/instructions about organ donation.

Increased awareness of the importance of advance directives has prompted various laws encouraging their use. Under the Federal Patient Self-Determination Act of 1991, hospitals are required to ask patients about advance directives and assist them if they wish to prepare an advance directive. In some jurisdictions, state law will require the custodian of an advance directive or the possessor of information about an advance directive to release information about the advance directive in response to proper requests for this information.

U.S. Living Will Registry of Westfield, N.J. operates a database where digital images of advance directives are centrally stored. In the traditional scheme, individuals that registered and stored their advance directives on this database have agreed in writting that the stored information will be made available to a wide class of service providers, such as hospitals, physicians, etc. Health care providers that are privileged subscribers to this registry have been able to automatically access database documents that were previously and independently registered by patients. Subscribers have obtained documents by using a secure Internet web site employing encrypted transmission, or by using automated telephone systems that send documents to registered facsimile machines. Non-subscriber health care providers have been able to obtain documents from the registry by calling and requesting the documents.

Traditionally, this registry placed all authority in the person executing the advance directive by virtue of a registration contract signed by the person. This approach did not take into account the fact that service providers such as hospitals often gain custody of these instruments without the benefit of a registration contract. Nevertheless, these service providers need to take appropriate steps to store and organize these instruments and, when appropriate, make them available on short notice, often during emergencies. The difficulty of this task is compounded when the service provider is part of a network of hospitals that want to deal with these advance directives cooperatively.

Referring to reference mostly filed after the commencement of the above noted operations by U.S. Living Will Registry, in U.S. Patent Application Publication No. U.S. 2003/0040939 a person can complete an advance directive and send it to a facility that will scan the document and store it in a database. Using a password, authorized users can access this information either over a telephone network or over the Internet. The information can be retrieved either by facsimile or by printing a document obtained over the Internet.

In International Publication No. WO 01/06436 advance directives can be scanned and stored in a central database for access by authorized individuals. A user can designate in advance a list of key institutions that will have access to this information. The system has "expert" features that check whether the stored directives comply with a relevant jurisdiction. See also U.S. Pat. No. 5,241,466.

In International Publication No. WO 02/37235 a participant is provided information and asked a number of questions regarding life planning issues, including questions about living wills. After all the information is supplied, information is stored in a database and can also be sent to a designated person. Information in this database can be accessed by "the client, the assigned caregiver(s)/person(s) listed in charge of future arrangements, the assigned attorney, the coroners office, and/or emergency medical personnel." Initiation, access, and continuation of the centralized data storage is controlled by the participant, although third party updates can be authorized.

In International Publication No. WO 01/99027 emergency personnel can identify a patient by scanning the iris of, or a transporter worn by, a patient. This identifying information is sent wirelessly over the Internet to a database that stores advance directives that are then retrieved and displayed to the emergency personnel.

In U.S. Patent Application Publication No. U.S. 2002/0196141 patient information can be stored on databases maintained by individual hospitals or on a central server. A system administrator can establish which subscribers have access and the level of access. Subscribers such as doctors, hospital personnel, insurance companies, etc. gain access to the database by using either a password or by presenting for scanning a token with a bar-code.

In U.S. Patent Application Publication No. U.S. 2002/0169638 a database of medical records can be accessed by a medical entity. The reference describes connecting to a database server through wireless devices having a range of 20 miles or more so that "medical facilities and providers can link together, thus sharing patient data and allowing for continuous access to the patient electronic record." Paragraph 14.

U.S. Patent Application Publication No. U.S. 2001/0034617 describes a system where hospitals or other cooperating companies can be authorized by a patient to gain access to medical records stored in a database. The hospitals and the patient must both register with this service.

In U.S. Patent Application Publication No. U.S. 2002/0029264 a hospital or other subscriber can send raw MRI image data for processing by a central server. The processed information can be sent back to a number of different hospitals designated by the originating hospital.

In U.S. Patent Application Publication No. U.S. 2002/0188467 patients, health-care providers, insurance companies, and pharmacies can gain access to patient information stored on a central server. Unauthorized access to the server is prevented by (1) employing hardwired business to business connections; (2) encrypting information sent over the Internet; (3) passwords; (4) compartmentalizing information by allowing a user access to only those portions of a patient's medical records that are necessary for the issue at hand; and (5) providing information on a CD-ROM.

In U.S. Patent Application Publication No. U.S. 2002/0103675 patient information may be stored by patient or by hospital and stored in a central database. Users such as patients, physicians, hospitals, pharmacies, etc. can gain access to the patient information.

In U.S. Patent Application Publication No. U.S. 2001/041991 medical records can be accessed over the Internet by a patient or by individuals authorized by the patient.

The description herein of some references having a publication or issuance date less than one year from the effective filing date of the present application, does not imply the reference is prior art, but is included simply to enhance the scope of applicant's disclosure. In this regard, see U.S. Patent Application Publication No. U.S. 2003/120527 (access to patient information over the Internet granted depending on the individuals' need for information); U.S. Patent Application Publication No. U.S. 2003/0101081 (surgeons individually or as a group can subscribe to a service that stores postoperative notes that are made available to them, hospitals, patients, anesthesiologists, etc.); U.S. Pat. No. 6,157,914 (a hospital can download centralized medical information from a different hospital, switching to different systems in order to gain access); U.S. Pat. No. 6,604,115 (cardiovascular data stored in a database is made available over a network either intrahospital or interhospital); and U.S. Pat. No. 6,574,742 (hospitals can outsource their picture archiving and communications systems (PACS) requirement by communicating over a network to a central database).

SUMMARY OF THE INVENTION

In accordance with the illustrative embodiments demonstrating features and advantages of the present invention, there is provided a method for storing and retrieving advance directives with a database coupled to a communications system. The method is performed on the initiative of a service provider, by registering and storing information about the service provider on the database in anticipation of future creation of advance directives that will come into at least the temporary possession of the service provider. The method also includes the step of storing on the database information supplied by the service provider about a person and the person's advance directive. Another step is automatically transmitting upon request by the service provider information about one or more advance directives that were stored in the database by the service provider.

In accordance with another aspect of the invention a system is provided for storing and retrieving advance directives. The system has a communications system, and a database coupled to the communications system. The database is arranged to register and store information about a service provider in anticipation of future creation of advance directives that will come into at least the temporary possession of the service provider. The database is arranged to store information supplied by the service provider about a person and the person's advance directive. The communications system is operable in response to a request by the service provider to automatically transmit information about one or more advance directives that were stored in the database by the service provider.

By employing systems and methods of the foregoing type, advance directives can be stored and retrieved in a highly efficient and effective manner. In one preferred embodiment, the system can be arranged to handle advance directives whether or not they are controlled by a written registration contract executed by the person covered by the advance directive. Such a system would allow a hospital to obtain possession of advance directives executed by hospital patients and store them as an electronic record in a central database that can be become a central repository for any hospital. Once stored in the central database, these advance directives can be made accessed by hospitals in the same network or, if proper under the recording guidelines, by any independent hospital or healthcare provider.

The preferred system can be operated so that advance directives are automatically released depending on predetermined rules. If documents are stored unaccompanied by a registration agreement executed by the party benefitted by the advance directive, they are placed into the originating facility's restricted collection and access to them is limited. The features listed below detail the various options by which access to the restricted documents are limited.

When a health care provider member is initially set up in the registry database, the criteria for that particular provider are entered. This includes a decision tree whereby a computer system checks to see whether access to that particular provider's restricted documents are controlled by (a) the state in which the document was registered, (b) the network of health care providers that the originating provider belongs to, and (c) the facility class of the originating facility (hospital, nursing home, hospice, doctor's office, etc.).

Restricted documents are always accessible to the originating provider. When a member provider other than the originating facility requests a restricted document, the system compares the Source ID Code of the requesting provider, with the Source ID Code of the facility listed for the requested document, and goes through the various options. The system will then either validate the request and send the document, or it will respond with a message that the documents exists, but is not accessible to the requesting provider. The requesting provider is then referred to the originating provider so that they may work out possible release of the document directly between the two providers.

If a state has a law prohibiting the withholding of an advance directive for any reason, the program permits advance directives registered from that state to be made available to any requesting provider.

The system also allows the sharing of restricted documents with all facilities within a health care network, such as a hospital system, even if such a system has facilities in different states.

The system also allows access to documents to be restricted to certain classes of facilities within the same network.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein.

DETAILED DESCRIPTION OF THE PREFERRED EMBODIMENTS

Figure 1:
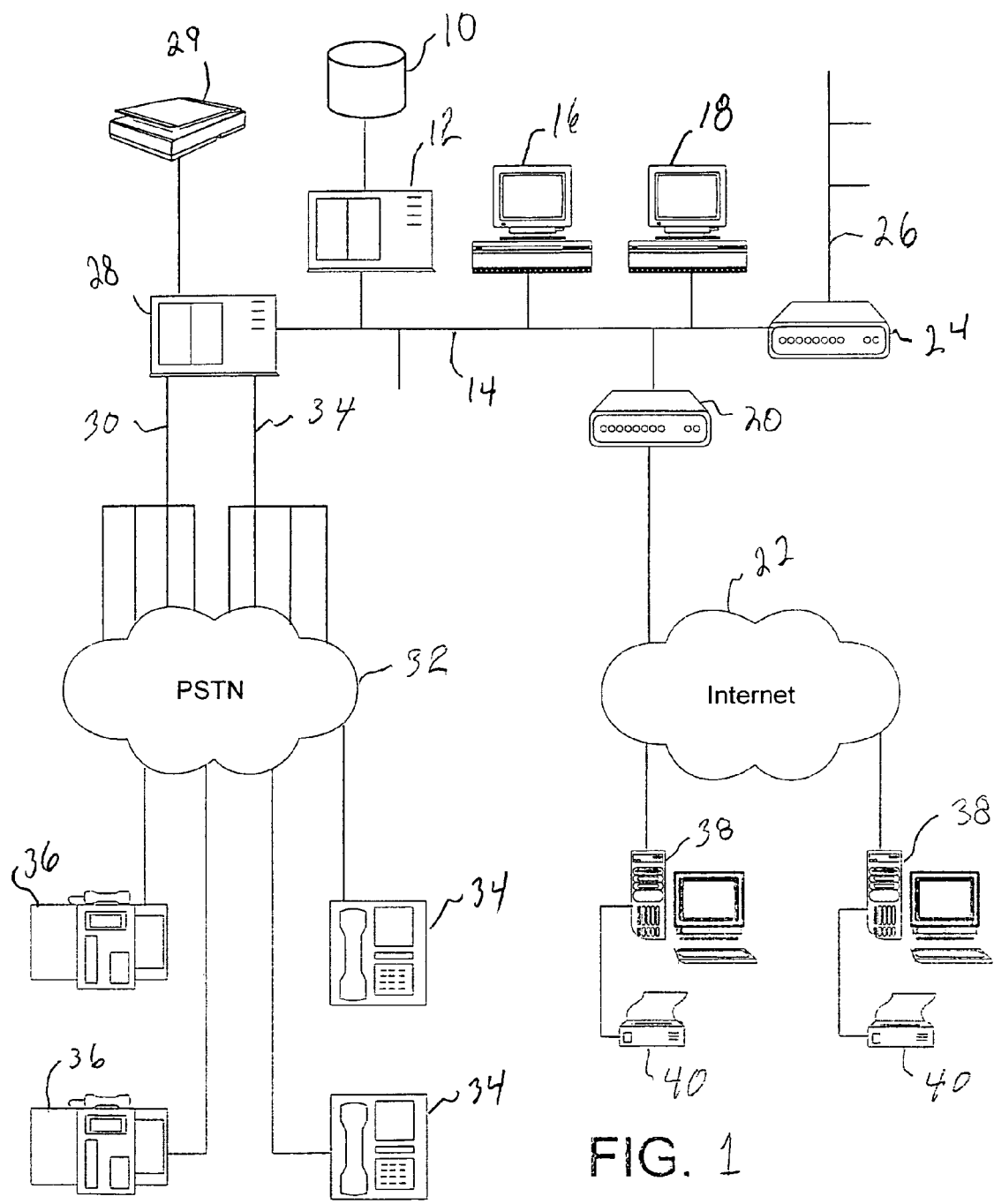
FIG. 1 is a schematic diagram of a system operable to perform a method in accordance with principles of the present invention.

Referring to FIG. 1, the illustrated schematic shows a system with a database 10 in the form of a mass storage device coupled to a computer 12. Computer 12 is connected to local area network 14, as are workstations 16 and 18. Network 14 also connects to internal local area network 26 through a router 24, which has a secure firewall.

Network 14 also connects to a communications system, shown herein as computer 28. Computer 28 has an input connected to a document scanner 29. Computer 28 includes a telephone messageing system shown connecting through a plurality of telephone lines 30 to the public switched telephone network 32. This messaging system is of the type that can respond to callers by providing an announcement offering a number of menu choices or prompts that are selected when the caller presses a specified key on the caller's touchtone telephone set 34. In a well-known manner, the caller can continue to select different options and work with computer-generated verbal instructions to navigate through a hierarchical menu.

The massaging system in computer 28 can respond to callers' touchtone selections by sending communications requests along network 14. In some instances the information returned along network 14 to computer 28, is recognized as a requested telephone number, and is used to place a call over one of the plurality of telephone lines 34 connected to telephone network 32. Also, the information returned along network 14 may contain image information that is processed by computer 28 and transmitted as a conventional facsimile signal over one of the plurality of telephone lines 34 to one of the facsimile machines 36.

Network 14 connects through router 20 to a global network 22, in this case, the Internet. Computer 12 (or computer 28, or some other computer (not shown) on network 14) can act as a web server so that third parties can use browsers running on their personal computers 38 to access the web services provided by this system. In particular, these personal computers 38 will have their own individual printers 40 that can be used to print information such as advance directives that are downloaded over the Internet 22 from the web server 12.

The preferred database 10 will contain a main table of persons/registrants sorted by social security number. The record for each person will include name, address, birthdate, telephone numbers, emergency contacts, as well as certain other markings or notations, signifying the existence of an advance directive, organ donation instructions, or a registration agreement. While the foregoing may be stored as text, this record can also include scanned digital images of a person's advance directive or other pertinent documents. These images can be stored in any one of various formats, although storage in TIFF format is preferred.

As described hereinafter, annotations in this main table that indicate the existence of a registration agreement will lead to open access to information in database 10 (including advance directives) to qualified recipients, such as health care providers that may be listed in the database 10 in another table (for example, a table of all the service care providers as described below). Also, the main table has notations indicating the state of origin, which will allow correlation with a jurisdiction table that lists jurisdictions that require open access. Using this stored information the system can determine if specific advance directives in the database 10 must be released under the laws of that jurisdiction.

Database 10 will also include a table of service providers that can be independent sources of advance directives prepared by persons. For example, hospitals may obtain from their patients advance directives that are then stored in the database 10. This table of service providers is preferably indexed by an eight digit service provider (source) ID code. The record for each service provider will include name, classification (hospital, physician, attorney, etc.), address, information about the contact person for this service provider, network affiliation, classification within the network, and web site, as well as certain notations or settings, such as active/inactive status, whether Internet access is permitted, whether information retrieval is permitted, whether retrieval restrictions exist, etc. This record will also be marked with notations or settings indicating whether access to information will be affected by applicable state law, membership in a network, or classifications within that network.

Since the foregoing contemplates that some service providers will be members of a network, the database 10 will also include a network table that lists the members of predefined common networks of service providers. The network table will include identifying information about the network and the identification code for each of its members. The network table will also contain information about whether individual members of the network are considered a qualified member; specifically, a classification code indicating individualized membership privileges. These privileges can include the ability to store or access information or documents on the database 10 or the ability to prepare reports about information on the database. These individualized membership privileges can also be further refined by granting individual members access to advance directives stored by other members based on classification within a predetermined group of class designations.

Other tables can also be included to identify network administrators with authority to make global changes affecting the network. This latter table can include the network identification number and the name, location, and telephone number of personnel authorized to act as an administrator. Using the foregoing, a group of hospitals may be virtually combined into a single network that will make available to all members of the same network, information stored in the database 10 by any member of the same network.

The database 10 can also have a staff table constituting a roster of staff members that are authorized by a service provider to gain access to the database. The staff table can include the name of the staff member, an employee identification number, and the identification number of the service provider. This table may also include information about the privileges that will be granted the staff member, based on a level designation code stored in the database 10. For example, the staff member can be allowed to upload or download information about advance directives, or may be given the ability to prepare status or activity reports. Such reports can be a chronological report identifying who accessed the database 10 and the type of activity performed during that episode. Other reports can include a listing of the advance directives stored by the service provider on the database 10 annotated with information concerning the frequency of access.

The database 10 may also have a table of classifications for service providers. This table may include such classifications as: hospital, physician, attorney, estate planner, nursing home, etc. Each classification may be marked with settings or notations signifying the privileges that will be allowed for that particular class. For example, some classes may be allowed to only upload and store information or documents, while other classes may also be allowed to access and download information and documents. These privileges may also be established by providing another table of qualified recipients (third parties) that are listed with specific privileges, such as the ability to get information or advance directives from the database 10 in accordance with predetermined transmission rules.

Figure 2:
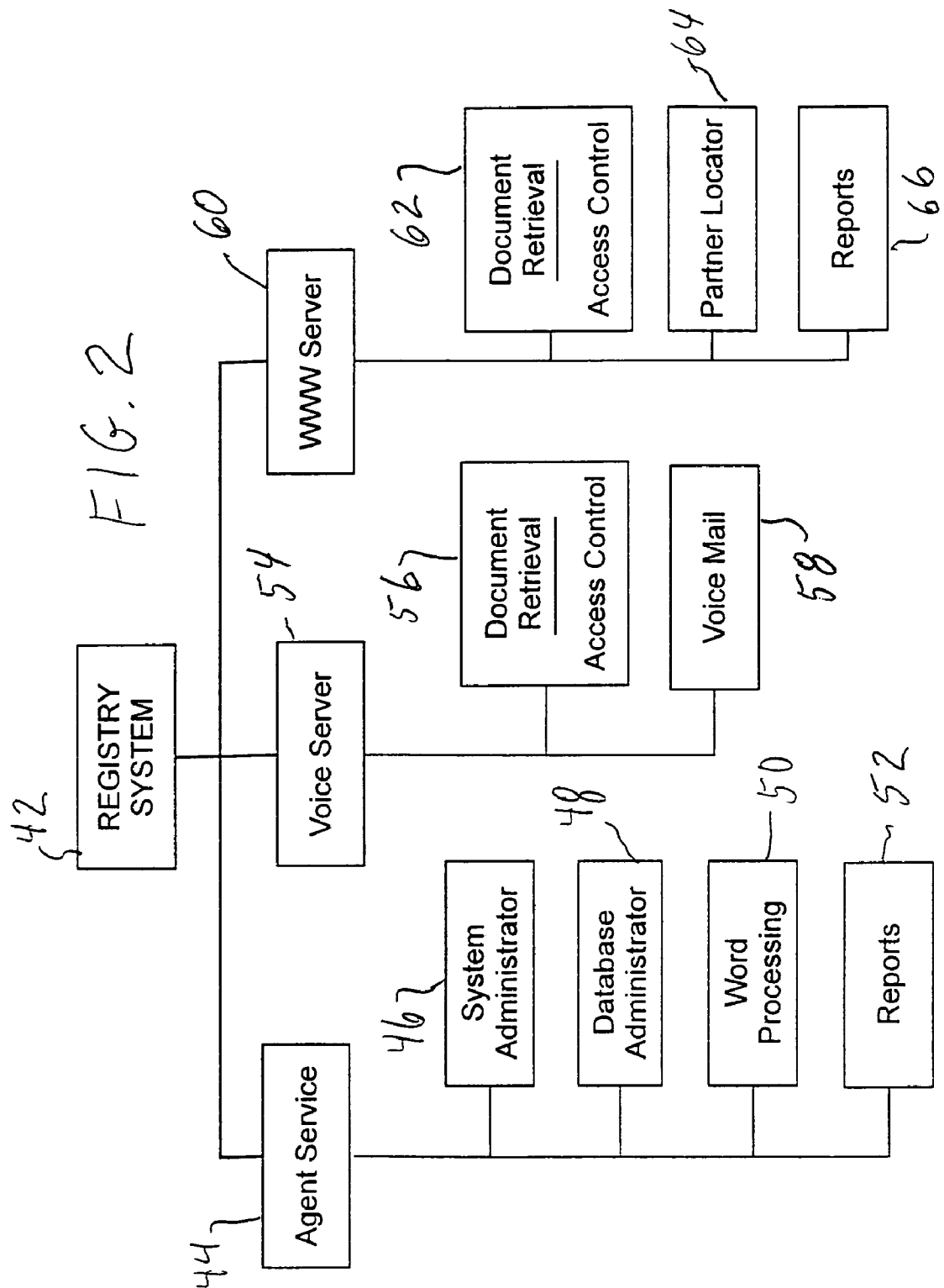
FIG. 2 is a logical diagram associated with the system of FIG. 2.

Referring to FIG. 2, the present registry system 42 is shown with three major services: agent service 44, voice server 54, and web server 60. Agent service 44 includes the system administration function 46 where a system administrator can deal with such issues as loading or updating software, modifying or adding hardware, adding users, assigning passwords, forming groups, establishing group and user permissions, establishing router domains, etc.

The database administration function 48 allows certain agents to control the database and to add, update, or remove records from the database. In particular, function 48 allows a database administrator to access and edit a table of agents. This agent table will be a list of individuals with passwords that allow them access to the database administration function. The agent table will include designations of the privileges that will be given to those individuals listed in the table.

Administration function 48 will allow an agent to add, update, or remove records about persons who have signed a registration contract that specifies the terms and conditions under which their advance directive or other information can be distributed to third parties.

In some instances information will be sent from a service provider such as a hospital, physician, estate planner, nursing home, etc. This information can include demographic information about a person who has executed an advance directive as well as a copy (traditional or electronic) of that advance directive. This information can be added to database 10 at a workstation 16 or 18 using administration function 48. This service provider can provide information about itself by filling out a traditional form that will then be added to the database 10 by using administration function 48. Instead of being added to database 10 manually as described above, in some instances information may be added by completing an electronic on-line application.

With administrative function 48, an agent can add, update, or remove records in the table of service providers. Function 48 can also be used to add, update, or delete records from a table of individuals that the service provider authorizes to access database 10, including the privileges granted to each such individual.

Database administration function 48 also includes a feature that allows an agent to obtain a new service provider identification number in case that number is needed before a record on that service provider is added to the database 10. Function 48 also includes a feature whereby an agent can automatically dispatch facsimile confirmation from computer 28 through telephone network 32 to a designated facsimile machine 36.

The database administration function 48 also permits an agent to add, update, or delete information about service providers with respect to a predefined network of providers. The agent can access all the service provider network records described above.

Whether information is supplied indirectly from a service provider or directly from an individual that executes a registration contract, the administration function 48 will allow an agent to scan an advance directive on scanner 29 (FIG. 1) to produce a digital image that will be uploaded directly into computer 28. Alternatively, an agent can import over network 14 a digital image file that was previously scanned and stored on another computer (e.g., on computers 16, 18, or 38 or on computers (not shown) connected to network 26). An agent can also remove a previously uploaded document image file. The registry system can also accept documents that are faxed to it. Faxed documents, when they are received by the computer 28, are converted by the computer 28 from fax format to TIFF and stored in that format. (They are later converted from TIFF to FAX when they are transmitted to a fax machine. They are transmitted to WWW clients as TIFF files, to be displayed by any available TIFF-viewer on the client PC.) Faxed documents are thus received and converted by computer 28, staff enter the identifying information associated with the document, and the document is uploaded into the database 10.

Also, function 48 allows the database administrator to define and modify a table of classes. Specifically, the class table can list classes such as: hospital, physician, estate planner, nursing home, etc. The database administrator can assign certain privileges to service providers depending upon their classification.

The agent service 44 also includes a work processing application 50 to enable creation of new documents or editing of existing forms that need to be sent to some person involved with the present system. Also included is a report generator 52 for providing statistics on records in various tables, chronological or summary reports on transactions for all or some clients, etc.

Voice server 54 is implemented in previously mentioned computer 28 of FIG. 1 and includes a voicemail function 58 of the usual type, as well as a document retrieval/access control function 56. Function 56 provides a dial-up facsimile service. Specifically, a user can call into one of the lines 34 (FIG. 1) to access the call massaging system of computer 28. As noted above, the caller can respond to various verbal prompts and use a telephone keypad to send a service provider identification number (or registrant number), an employee ID number if applicable, a password, the social security number of a person that may have an advance directive, and any other information that may be needed by the system. In response, the massaging system will check the privileges afforded the caller and if appropriate respond by sending by facsimile over network 32 a copy of the advance directive requested.

System 42 also has a web server 60, which is implemented by previously mentioned computer 12 (FIG. 1) and includes a document retrieval/access control function 62. Function 62 provides web based access to database documents.

For security, if a hospital or health system has a local network, they usually have a method whereby authorized employees go through an authentication process to gain access to that network. When such a network exists, the present registry system utilizes it as follows: The registry system is set up so that only those employees that are already authenticated on the provider's local network, can gain access to the system. Once an authorized employee is authenticated for access to the local network, and then attempts to gain access to the registry system, computer 12 then checks that employee identifier against its table to see if that employee is authorized to access the registry system and to determine at what privilege level they may access the registry system (access and reports, or just access). In this way, an employee could not access the registry system from a home computer or any computer other than those through which they can gain access to the provider's local network. Of course, if the provider does not have such a local network, this does not apply.

With web based access, the browser on one of the personal computers 38 (FIG. 1) can access a web page offered by server 12 and then login by typing a service provider identification number (or registrant number), an employee ID number if applicable, a password, the Social Security number of a person that may have an advance directive, and any other information that may be needed by the system. If the login is successful and the user has been granted the privilege to access database 10, web server 12 can send over Internet 22 an image of an advance directive stored in database 10. Once this image is displayed on personal computer 38, the user's browser can be directed to print the displayed advance directive on printer 40.

Function 64 can be used by the public to locate a local agent (attorney, hospital, etc) for assistance in preparing and/or registering an advance directive. Local agents who have made arrangements with the registry system operator to provide this service are referred to elsewhere as "partners" of the registry.

Function 66 allows the service provider to prepare chronological reports showing activity by various individuals, or reports showing the entry dates and revision dates of various documents uploaded by the service provider.

To facilitate an understanding of the principles associated with the foregoing apparatus, its operation will be briefly described. It will be assumed that access to the database 10 will be sought over the Internet 22 using a browser on one of the personal computers 38 (FIG. 1). If a hospital or other health system is gaining access through a local network, they usually have a method whereby authorized employees go through an authentication process to gain access to that network, as described above. The published URL of the home web page of web server 12 will be entered into the browser of personal computers 38 in the usual fashion. In response, web server 12 will send a home web page using the hypertext transmission protocol (HTTP).

If the user has not previously registered as a service provider, the user will be given the option to register and will be directed to a web page requesting the details necessary to register as a service provider. The user will enter the information noted above to complete a record for this service provider. In some cases the user will be in a network of service providers, for example, a network of hospitals. In that case, the user will need to enter a record for each member of the network together with the identity of the network administrator(s) authorized to edit or update the global parameters associated with the network.

The user will be given an identity code for each service provider as well as an identity code for the network. The user can also identify individuals that will be allowed access to the system with privileges that are designated in advance. Each such individual will be given a user number and password (personal identification number or PIN). In addition, the user can specify certain classes of users and designate the privileges that will be granted each such class. To complete this classification, user will then assigned class codes to each user number.

All the foregoing assumed that information was being supplied online. However, in some instances the user will complete a conventional paper application and send the completed form by mail or facsimile so that a central operator of the system can manually place the information into the database 10 in order to register a service provider with the system.

Figure 3:
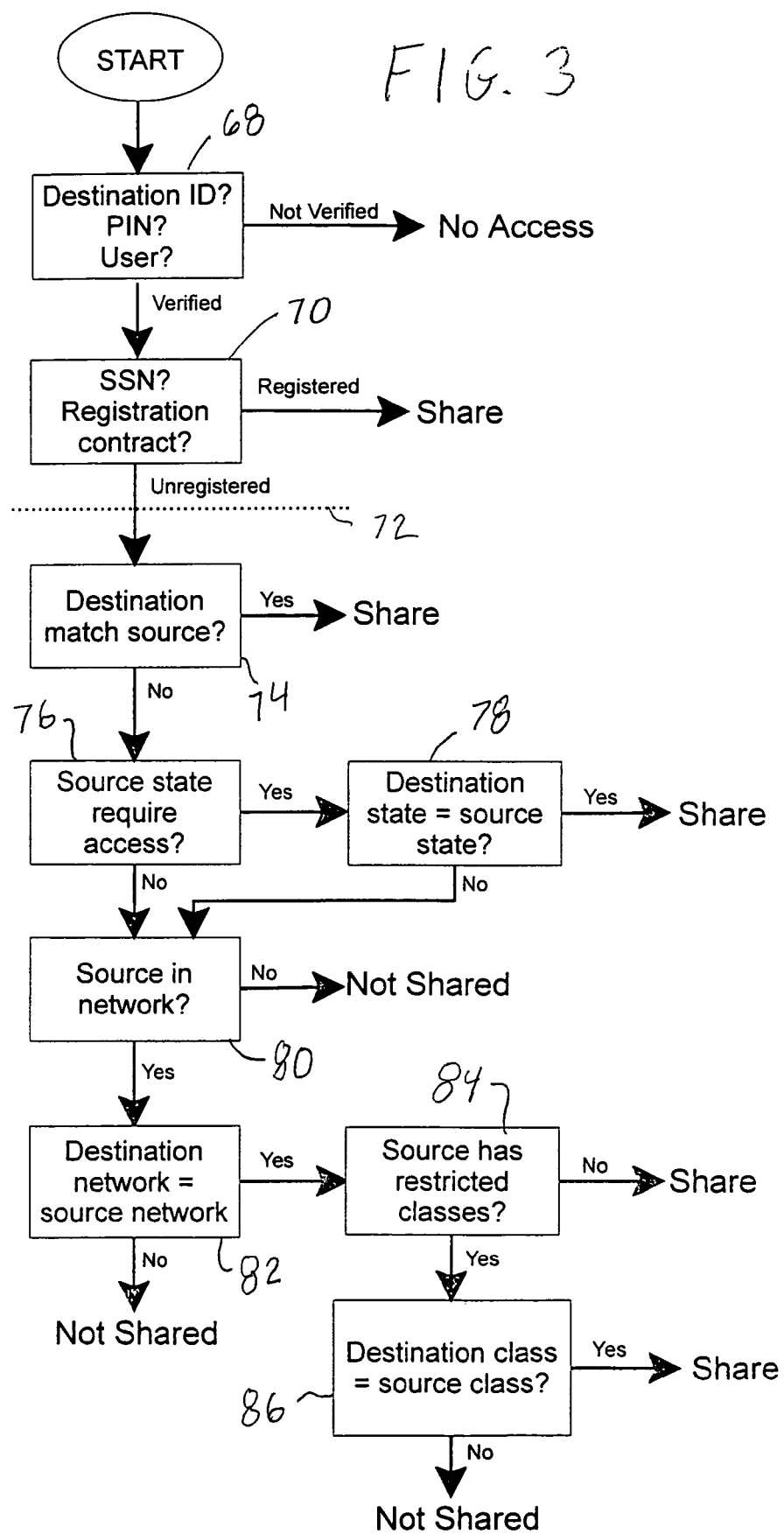
FIG. 3 is a flowchart associated with the system of FIGS. 1 and 2.

Once the registration process has been finished, an individual with a user number and password can now login and gain access to the system. As indicated in step 68 of the flowchart of FIG. 3, the user will supply the identification code of the service provider (destination ID), together with a user number and password (PIN). In this flowchart the identification code of the service provider is described as a "destination ID" to indicate that documents may soon be requested and that these documents will be sent to the destination associated with the identification number supplied during login. If the information supplied by the user at step 68 does not coincide with information previously recorded in database 10 access will be denied, but otherwise step 70 will be executed.

In step 70 the user will be asked to supply the social security number of an individual whose advance directive may have been previously recorded in the database 10. Computer 12, now acting as a database server, will look up records in the main table, which records are indexed by social security number. Assuming a matching record is found, computer 12 will now fetch this record and check to see whether the fetched record has been annotated as being controlled by a registration contract. In this embodiment the existence of a registration contract means that the person associated with the social security number has agreed to release his or her information in the database to a broad class of health care providers, including health care providers that may be registered subscribers to the system and entitled to use the system's automated features. Accordingly, information in database 10 will be released when a registration contract exists, otherwise step 74 will be executed.

Step 74 and subsequent steps are indicated as being beyond the boundary 72, signifying that decisions to release information will be controlled by terms and conditions established by a service provider, that is, an entity other than the individual that executed one of the advance directives that are stored on database 10. In step 74 computer 12 determines whether the destination ID (the identification code for the service provider seeking information) matches the source ID (the identification code for the service provider that originally supplied the information being sought). Basically, computer 12 examines the fetched record to determine whether that record is marked with a source ID indicating the information was supplied from the service provider that is now making an inquiry. In the preferred system, the service provider that supplied information is always given access to the information that it originally supplied. If a service provider other than the originating source is making the request, then control is transferred to step 76.

In step 76 computer 12 examines the fetched record and determines its state of origin. In the preferred embodiment the state of origin is considered the state of the service provider that originally supplied the information, although in other embodiments the state of origin can be the state of residence of the person described in the fetched record. This state of origin is compared to a table of jurisdictions that require open access by law. If the state of origin is not found in this table of jurisdictions control is transferred to step 80, but if the state of origin is found control is transferred to step 78.

In step 78 rules established by the operator of the registry system are invoked to determine whether information must be released under the laws of the state of origin. In one embodiment computer 12 will release information when the state of origin matches the state of the service provider seeking information. In other embodiments more complex rules of disclosure may be employed. For example, some jurisdictions may require release of information for documents that were generated in that jurisdiction without regard to whether the request comes from outside the jurisdiction. In such a case, computer 12 will release information whenever the state of origin corresponds to such a jurisdiction. Other rules may be implemented to accommodate various laws that may be promulgated in other jurisdictions. If however, no controlling jurisdictional law is indicated, then control is transferred to step 80.

In step 80 computer 12 examines the records associated with the service provider seeking information and determines whether that provider is a member of a network of providers. If not, information is not provided, otherwise control is transferred to step 82.

In step 82 computer 12 determines the network affiliation indicated in the records associated with the service provider that originally supplied the information being currently sought. If the service provider seeking information is not part of the same network as the service provider that originally supplied the information access is denied, otherwise control is transferred to step 84.

In step 84 computer 12 checks the records associated with the service provider seeking information to determine if its record is annotated as implementing class restrictions. If no class restrictions are indicated access is granted, otherwise control is transferred to step 86.

In step 86 computer 12 compares the class numbers marked in the records of the service provider seeking information and the service provider that originally supplied the information. In one embodiment, if these class numbers are the same access is granted, otherwise access is denied. In other embodiments classes can be arranged in a hierarchy so that the service provider seeking information will always be granted access to information originally supplied by a service provider of the same or lower rank. Alternatively, some service providers can be given a high rank that allows access to any other class of records; or a low rank that allows access by every other class of information seeker.

If information is denied, computer 12 will display a message stating whether information is stored in database 10 for the social security number in question and will give further information on how to go about contacting someone who can help get the information requested.

Assuming however the service provider seeking information is granted access, computer 12 will display a screen giving appropriate text data gathered from the database 10. The user can now click on an icon to display the digital images stored in database 10. This digital image may be an advance directive such as a living will, health care proxy, etc. The user may now print the image on printer 40 using the printing facilities typically associated with conventional browsers. In some embodiments, the user may request that the advance directive be sent by facsimile, in which case computer 28 will fetch the digital image, convert it into a facsimile signal, make a connection through telephone network 32, and send the signal to one of the facsimile machines 36. Computer 28 will only send information to facsimile numbers that have been prerecorded in database 10 as a number authorized by the service provider in question.

It will be appreciated that the facsimile can also be transmitted in response to instructions sent by using telephone 34 to respond to verbal prompts from the massaging system of computer 28.

The foregoing system would work well as a national federal system for managing advance directives, allowing storage and retrieval of documents as overseen by a federal agency while respecting and complying with the various state statutes already in place.

It will be appreciated that various modifications may be implemented with respect to the above described, preferred embodiment. In some embodiments the database can be a distributed database located in different localities with a steering system that allows requests to be directed to the appropriate locality. Also, the records of various individuals and entities can include a greater or lesser amount of information depending upon the specific applications. While an Internet connection is illustrated, other systems may employ private networks, virtual private networks, satellite links, closed cable systems, or the like, that communicates with any number of protocols. Also embodiments are contemplated where documents supplied by a service provider can be directly accessed by the person described in the document, and vice versa. It will also be appreciated that networks can be formed among entities of different types, for example, a network including hospitals and estate planners. Also, these networks need not be part of a single business entity but may be a loose confederation that wishes to share information. Also, ti will be appreciated that systems that implement rules to accommodate open access laws of some justifications may be implemented by equipment that is located in an unrelated jurisdiction. Also, embodiments are contemplated where service providers can generate their own user-defined rules for granting access to their own staff members, to network affiliates, or to service providers with whom no pre-existing relationship was ever formed.

Obviously, many modifications and variations of the present invention are possible in light of the above teachings. It is therefore to be understood that within the scope of the appended claims, the invention may be practiced otherwise than as specifically described.

The invention claimed is:

1. A method for storing and retrieving advance directives with a database coupled to a communications system, comprising the steps of:

on the initiative of a service provider, registering and storing information about the service provider on the database in anticipation of further creation of advance directives that will come into at least the temporary possession of the service provider;

storing on the database information supplied by the service provider about a person and the person's advance directive;

automatically transmitting upon request by the service provider information about one or more advance directives that were stored in the database by the service provider; and processing a request for automatic transmission of information about a specific advance directive made by a requester other than the service provider that supplied information about that specific advance directive by determining if the requester has been previously recorded in the database as being a qualified member of one of a plurality of predefined common networks previously recorded on the database, and if so recorded (a) granting the request if the requester and the service provider cohabit a common one of the common networks that includes the requester and the service provider, and (b) denying the request if the requester and the service provider do not cohabit a common one of the common networks that includes the requester and the service provider, notwithstanding that the requester has been previously recorded in the database as a qualified member of another one of the predefined common networks.

2. A method according to claim 1 comprising the step of:

prerecording in the database, classifications for members of the predefined network, the step of granting a request if the requester is part of the predefined network being performed by determining if the requester is classified in the database as qualified to have requests for advance directives granted.

3. A method according to claim 2 wherein the step of prerecording classification is performed by:
listing members of the predefined network in the database with a class designation signifying individualized membership privileges, said privileges being settable to include: (a) obtaining advance directives; and (b) recording advance directives in the database.

4. A method according to claim 3 wherein said individual membership privileges being settable to include: (a) creating reports on activity in, or status of, the predefined network; and (b) access to advance directives stored by members in a predetermined group of class designations.

5. A method according to claim 1 comprising the step of:
obtaining authorization from a registrant to store and release information about an advance directive executed by the registrant to a specified class of entities; and
storing on the database information supplied by the registrant about the registrant's advance directive; and
granting a request from one of the specified class of entities for automatic transmission of information about the registrant's advance directive.

6. A method according to claim 1 wherein the person is a hospital patient of the service provider, the step of storing on the database comprises the steps of:
providing to the person, through the service provider, information about advance directives; and
obtaining possession of the advance directive from the person before performing the step of storing on the database information supplied by the service provider about the person and the person's advance directive.

7. A method according to claim 1 wherein the step of storing on the database comprises the steps of:
providing to the person, through the service provider, information about advance directives; and
obtaining possession of the advance directive from the person before performing the step of storing on the database information supplied by the service provider about the person and the person's advance directive.

8. A method according to claim 7 wherein the step of automatically transmitting information is performed by downloading information from the database over a global network.

9. A method according to claim 7 wherein the step of automatically transmitting information is performed by either (a) downloading information from the database over a global network, or (b) facsimile transmission of information from the database over a telephone network.

10. A method according to claim 9 comprising the step of:
prerecording on the database a facsimile telephone number associated with the service provider to be used when transmitting information from the database to the service provider.

11. A method according to claim 10 wherein the step of automatically transmitting information is performed in response to requests sent either (a) over a global network using a browser, or (b) over a telephone network using a telephone to respond to verbal prompts sent by the communications system.

12. A method according to claim 9 wherein the step of storing on the database is performed by scanning the person's advance directive and storing a digital image produced thereby on the database.

13. A method according to claim 9 comprising the step of:
automatically transmitting upon request by a third party other than the service provider information about one or more advance directives that were stored in the database by the service provider, provided the identity of said third party is recorded in the database and provided such transmission is in accord with predetermined transmission rules.

14. A method according to claim 1 comprising the step of:
prerecording in the database a roster of staff members of the service provider with a level designation signifying individualized authority levels, said authority levels being settable to include: (a) obtaining advance directives, (b) recording advance directives in the database, and (c) creating status and activity reports from information in the database.

15. A method according to claim 1 comprising the step of:
granting a request for automatic transmission of information about a specific advance directive made by a requester other than the service provider that supplied information about that specific advance directive if the specific advance directive has been recorded with a notation signifying that an applicable jurisdiction requires release of the specific advance directive in response to properly made requests.

16. A method according to claim 1 comprising the steps of:
granting a request for automatic transmission of information about a specific advance directive made by a requester other than the service provider that supplied information about that specific advance directive if (a) the specific advance directive has been recorded with a notation signifying that an applicable jurisdiction requires release of the specific advance directive in response to properly made requests, or (b) the requester has been previously recorded in the database as being a qualified member of a predefined common network that includes the requester and the service provider.

17. A method according to claim 16 comprising the step of:
in instances where the requester will be denied automatic transmission of information about the specific advance directive, notifying the requester of the existence in the database of information about the specific advance directive and how to obtain information about it.

18. A method according to claim 1 comprising the steps of:
granting a request for automatic transmission of information about a specific advance directive made by a requester other than the service provider that supplied information about that specific advance directive if (a) the specific advance directive has been recorded in the database with a notation signifying that an applicable jurisdiction requires release of the specific advance directive in response to properly made requests, (b) the requester has been previously recorded in the database as being a qualified member of a predefined common network that includes the requester and the service provider, or (c) the specific advance directive has been recorded in the database with a notation signifying that it can be released if the requester has been granted entry to a list of qualified recipients recorded in the database.

19. A system for storing and retrieving advance directives comprising:
a communication system; and
a database coupled to said communications system, said database being arranged to register and store information about a service provider in anticipation of future creation of advance directives that will come into at least the temporary possession of the service provider, said database being arranged to store information supplied by the service provider about a person and the person's advance directive, the database being structured to store a table of qualified members arranged in a plurality of predefined common networks, said communications system being operable in response to a request by the service provider to automatically transmit information about one or more advance directives that were stored in the database by the service provider, said communications system being operable to automatically transmit information about a specific advance directive made by a requester other than the service provider that supplied information about that specific advance directive if the requester has been previously recorded in the database as being a qualified member of one of the predefined common networks, and if so recorded (a) granting the request if the requester and the service provider cohabit a common one of the common networks that includes the requester and the service provider, and (b) denying the request if the requester and the service provider do not cohabit a common one of the common networks that includes the requester and the service provider, notwithstanding that the requester has been previously recorded in the database as a qualified member of another one of the predefined common networks.

20. A system according to claim 19 wherein the database is prerecorded with classifications assigned to members of the predefined network, the communications system being operable to automatically transmit information if the requester is classified in the database as qualified to receive advance directives.

21. A system according to claim 20 wherein the database is arranged with a table of members of the predefined network with a class designation signifying individualized membership privileges, said privileges being settable in the database to include: (a) obtaining advance directives; and (b) recording advance directives in the database.

22. A system according to claim 21 wherein said individual membership privileges being settable in the database to include: (a) creating reports on activity in, or status of, the predefined network; and (b) access to advance directives stored by members in a predetermined group of class designations.

23. A system according to claim 19 wherein the database has some of its records marked to signify open access to health care providers, said communications system being operable in response to a request from a health care provider to automatically transmit information about advance directives marked for open access.

24. A system according to claim 19 wherein the communications system is operable to download from the database onto a global network information requested by the service provider.

25. A system according to claim 19 wherein the communications system is operable in response to requests from the service provider to either (a) download information from the database over a global network, or (b) facsimile transmit information from the database over a telephone network.

26. A system according to claim 25 wherein the database is prerecorded with a facsimile telephone number associated with the service provider and to be used when transmitting information from the database to the service provider.

27. A system according to claim 26 wherein the communications network is operable to automatically transmit information in response to requests sent either (a) over a global network using a browser, or (b) over a telephone network using a telephone to respond to verbal prompts sent by the communications system.

28. A system according to claim 25 wherein the database is arranged to store scanned digital images of the person's advance directive.

29. A system according to claim 25 wherein the database is arranged to store the identity of one or more third parties, said communications system being operable to automatically transmit upon request by one of the third parties other than the service provider information about one or more advance directives that were stored in the database by the service provider, provided the identity of said third party is recorded in the database and provided such transmission is in accord with predetermined transmission rules stored on the database.

30. A system according to claim 19 wherein the database is prerecorded with a roster of staff members of the service provider with a level designation signifying individualized authority levels, said authority levels being settable to include: (a) obtaining advance directives, (b) recording advance directives in the database, and (c) creating status and activity reports from information in the database.

31. A system according to claim 19 wherein the communications system is operable to automatically transmit information about a specific advance directive made by a requester other than the service provider that supplied information about that specific advance directive if the specific advance directive has been recorded in the database with a notation signifying that an applicable jurisdiction requires release of the specific advance directive in response to property made request.

32. A system according to claim 19 wherein the communications system is operable to automatically transmit information about a specific advance directive made by a requester other than the service provider that supplied information about that specific advance directive if (a) the specific advance directive has been recorded with a notation signifying that an applicable jurisdiction requires release of the specific advance directive in response to properly made requests, or (b) the requester has been previously recorded in the database as being a qualified member of a predefined common network that includes the requester and the service provider.

33. A system according to claim 32 wherein the communications system is operable in instances where the requester will be denied automatic transmission of information about the specific advance directive, to notify the requester of the existence in the database of information about the specific advance directive and how to obtain information about it.

34. A system according to claim 19 wherein the communications system is operable to automatically transmit information about a specific advance directive in response to a request by a requester other than the service provider that supplied information about that specific advance directive if (a) the specific advance directive has been recorded in the database with a notation signifying that an applicable jurisdiction requires release of the specific advance directive in response to properly made requests, (b) the requester has been previously recorded in the database as being a qualified member of a predefined common network that includes the requester and the service provider, or (c) the specific advance directive has been recorded in the database with a notation signifying that it can be released if the requester has been granted entry to a list of qualified recipients recorded in the database.

* * * * *